US009676678B1

(12) United States Patent
Agee et al.

(10) Patent No.: US 9,676,678 B1
(45) Date of Patent: *Jun. 13, 2017

(54) RENEWABLE FUELS CO-PROCESSING

(75) Inventors: Kenneth L. Agee, Tulsa, OK (US); Mark A. Agee, Jenks, OK (US); Rafael Espinoza, Tulsa, OK (US); Kym Brian Arcuri, Tulsa, OK (US)

(73) Assignee: Emerging Fuels Technology, Inc., Tulsa, OK (US)

( * ) Notice: Subject to any disclaimer, the term of this patent is extended or adjusted under 35 U.S.C. 154(b) by 653 days.

This patent is subject to a terminal disclaimer.

(21) Appl. No.: 13/529,599

(22) Filed: Jun. 21, 2012

Related U.S. Application Data

(60) Provisional application No. 61/499,545, filed on Jun. 21, 2011.

(51) Int. Cl.
*C07C 1/24* (2006.01)
*C07C 11/02* (2006.01)
*C07C 11/04* (2006.01)

(52) U.S. Cl.
CPC .............. *C07C 1/24* (2013.01); *C07C 11/04* (2013.01)

(58) Field of Classification Search
USPC ....... 585/254, 303, 240, 241, 242, 250, 252, 585/257, 275, 300, 310, 314, 330, 379, 585/440; 208/17, 78
See application file for complete search history.

(56) References Cited

U.S. PATENT DOCUMENTS

| | | | |
|---|---|---|---|
| 4,992,605 | A | 2/1991 | Craig et al. |
| 5,506,272 | A | 4/1996 | Benham et al. |
| 7,928,273 | B2 | 4/2011 | Bradin |
| 7,982,079 | B2 | 7/2011 | Marker et al. |
| 9,062,257 | B1 * | 6/2015 | Agee .......................... C07C 1/04 |
| 2008/0110080 | A1 | 5/2008 | Ansell et al. |
| 2008/0275278 | A1 | 11/2008 | Clark |
| 2009/0229174 | A1 | 9/2009 | Brady et al. |
| 2009/0287029 | A1 | 11/2009 | Anumakonda et al. |
| 2009/0294324 | A1 * | 12/2009 | Brandvold et al. ............. 208/17 |
| 2009/0300971 | A1 | 12/2009 | Abhari et al. |
| 2009/0301930 | A1 | 12/2009 | Brandvold et al. |
| 2010/0031572 | A1 | 2/2010 | Ansorge et al. |
| 2010/0069690 | A1 | 3/2010 | Gudde |
| 2010/0223839 | A1 * | 9/2010 | Garcia-Perez et al. ......... 44/313 |
| 2010/0317903 | A1 | 12/2010 | Knuuttila |
| 2010/0331586 | A1 | 12/2010 | Hanks et al. |
| 2011/0071327 | A1 | 3/2011 | Abhari et al. |

(Continued)

*Primary Examiner* — Prem C Singh
*Assistant Examiner* — Chantel Graham
(74) *Attorney, Agent, or Firm* — Head, Johnson, Kachigian & Wilkinson, PC

(57) ABSTRACT

A gas to liquids process with a reduced $CO_2$ footprint to convert natural gas and a renewable feed stock material into fuels or chemicals. In one non-limiting embodiment of the invention, a natural gas feed is converted into synthesis gas containing hydrogen and carbon monoxide. A minor portion of the hydrogen is thereafter extracted from the synthesis gas. The synthesis gas is converted to hydrocarbons in a Fischer Tropsch reaction. The Fischer Tropsch hydrocarbon product and a renewable feedstock are hydro processed with the extracted hydrogen in order to produce fuels and/or chemicals. Waste products from the renewable feed are recycled to produce additional synthesis gas for the Fischer Tropsch reaction.

12 Claims, 2 Drawing Sheets

(56) References Cited

U.S. PATENT DOCUMENTS

| | | |
|---|---|---|
| 2011/0113676 A1 | 5/2011 | Mackay et al. |
| 2011/0155631 A1 | 6/2011 | Knuuttila et al. |
| 2011/0172475 A1* | 7/2011 | Peters ................ C07C 1/24 585/254 |
| 2011/0178185 A1 | 7/2011 | Blevins et al. |
| 2011/0230632 A1* | 9/2011 | Abhari ............ C08F 36/06 526/335 |
| 2012/0208902 A1* | 8/2012 | Kresnyak ............ C10G 2/30 518/702 |

* cited by examiner

RENEWABLE FUELS CO-PROCESSING

CROSS-REFERENCE TO RELATED APPLICATIONS

This application claims priority to U.S. Provisional Application No. 61/499,545, filed Jun. 21, 2011, which is herein incorporated by reference.

BACKGROUND OF THE INVENTION

1. Field of the Invention

The present invention relates to a process to co process renewable feedstock materials with a gas to liquids process wherein at least a portion of hydrogen used to process the renewable materials is produced in a gas to liquids process.

2. Prior Art

Mixtures of triglycerides and fatty free acids can be hydro processed to produce chemicals and fuels, such as jet and diesel fuel. Sources of renewable feed can be seed oils, crop oils, animal fats, recycled greases and oils including soy oil, jatropha, camalina, palm oil, yellow grease, and other natural materials. The processing of these materials requires a considerable volume of hydrogen. Byproducts include $CO_2$, water, propane and light hydrocarbons. These natural feed materials are generally considered to be a renewable resource and are increasingly desirable to produce fuels in a sustainable manner. The production and use of fuels made from these resources also result in a very low production of greenhouse gases.

Triglyceride feeds have been converted to fuels via a trans esterification reaction with methanol to make biodiesel for many years. This process is becoming less desirable as it produces a lower quality fuel. These same renewable feedstocks can be converted to high quality fuels by processing with hydrogen over a catalyst. This has been practiced as a standalone operation or by co processing in a conventional refinery.

The present invention provides a novel process to convert renewable feed materials to fuels and chemicals by integrating operations with a Gas to Liquids process.

A gas to liquids (GTL) process integrates several process steps to convert natural gas into fuels and/or chemicals.

First natural gas is reacted with steam and/or oxygen to produce synthesis gas comprising carbon monoxide and hydrogen. This is a high temperature reaction involving a complex series of reforming and combustion reactions. This step is typically catalytic and performed in a Steam Methane Reformer (SMR) or an Autothermal Reformer (ATR). This step can also be accomplished non-catalytically in a Partial Oxidation reactor. A preferred method of the present invention is to use an ATR.

The synthesis gas produced in the first step is cooled and cleaned before further use. This may also include adjusting the H2: CO ratio to accommodate downstream requirements. The second step in the GTL process is conversion of the synthesis gas to hydrocarbon products. This is typically a Fischer Tropsch reaction carried out over an iron based or cobalt based catalyst. The reactor can be a fixed bed, fluidized bed, ebulating bed, micro channel or slurry bubble column reactor. The catalyst and reactor must be carefully matched to account for synthesis gas and product concentrations and heat transfer limitations to operate at the desired performance. The third step of the GTL process is to upgrade the raw hydrocarbon products from the Fischer Tropsch reactor to produce one or more products that meet a defined specification. For example if a middle distillate fuel is the desired product it could be refined to meet ASTM D-975 specifications.

The three key steps of the GTL process are integrated with utilities such as oxygen production, power generation, water treating, steam production and hydrogen management to meet the objectives of a specific plant design. The GTL process also requires additional infrastructure such as safety systems, flares, tanks, loading facilities to transport products and maintenance facilities etc.

The objective of the present invention is to use the GTL process to leverage production of renewable products. This can be done with any GTL process but a preferred embodiment is to utilize small modular GTL. Small as used herein is defined as 500 to 5,000 BPD. The reason for this preference is the relative size of typical renewable feedstock options. Renewable materials are typically available in limited quantities at any given location for example 500 to 1,000 BPD. For a small modular GTL plant this is a good fit and the co processing of the renewable feed can be advantageous to the GTL plant. For large 50,000 to 100,000 BPD plants the relatively small volumes of renewable materials are too small to make a significant contribution to the plant production.

There is currently a good deal of interest in production of renewable fuels. One method of producing renewable fuels is to gasify a raw renewable carbonaceous material to produce synthesis gas and use a Fischer Tropsch reaction to produce hydrocarbon products for upgrading. The chemistry of this process is essentially the same as a GTL process but the process is much more complex. In the case of a renewable biomass feed it is typically an irregular shaped solid material that must be stored on site, fed by auger or screw into a gasifier which typically operates at lower pressure. The resulting synthesis gas must then be compressed and can have a variety of contaminants such as sulfur and halogen compounds, minerals, tars, particulates and ash that must be removed to very low levels required by the Fischer Tropsch catalyst. By comparison, natural gas flows into a GTL plant under pressure. It has a well-defined composition with relatively few contaminants and commercial proven methods for cleanup. Commercial SMR's and ATR's have demonstrated operation at intermediate pressure (20-40 bars) which is ideal for Fischer Tropsch operation without further compression.

Another method to produce renewable fuels is to hydro process a renewable fat or oil such as crop oils, animal fats, algae oils or a polymer such as recycled plastics. These materials can be processed with hydrogen to reduce the oxygen content and/or molecular weight thus deriving a marketable hydrocarbon product. One of the challenges for processing these materials is the availability of hydrogen. Hydrogen is expensive to produce and requires significant infrastructure.

The objective of the present invention is to utilize the infrastructure and resources of a GTL process, preferably a small modular GTL process to co process renewable feedstocks. Four key elements of the integrated process result in improved efficiency and economics;

1. Hydrogen from the GTL process. A typical SMR produces a synthesis gas with a H2: CO ratio of 3:1. A typical ATR produces a ratio of 2.2 to 2.6:1. Methane as a feedstock has a very high H2: C ratio (2:1) compared to a biomass feed which is typically closer to 1:1. Therefore, natural gas converted to synthesis gas by the best available technology in the highest efficiency possible will typically have excess H2 greater than the 2:1 ratio required by the Fischer Tropsch reaction. This hydrogen can be removed and purified for downstream processing such as upgrading Fischer Tropsch products and co processing of renewable products.

2. GTL infrastructure—A GTL plant will have a significant amount of utilities and infrastructure that can be leveraged for co processing a renewable feed. If the renewable feed is processed in a standalone plant significant infrastructure would be required. Most of this infrastructure is already in place with the GTL plant with few additions required for the incremental co processing load.

3. Waste utilization—Hydro processing of the renewable feed results in loss of product as the glycerides are decomposed into CO, CO2, H2O and light hydrocarbons. In a standalone plant producing fuels from these feeds the waste products cannot be recycled. Some of the waste can be collected as LPG but it has lower value. In the integrated process of the present invention these waste products, which can be as much as 15% of the feed, can be recycled to the reformer for production of synthesis gas which can then be converted to products. This renewable material now becomes part of the Fischer Tropsch product.

4. Reduced CO2 footprint—The integrated process of the present invention results in a reduced level of CO2 added to the atmosphere for the volume of products produced. By recycling waste products from the hydro processing of the renewable feed a portion of the synthesis gas and hence a portion of the Fischer Tropsch products are based on carbon from the renewable source. While the Fischer Tropsch products are predominately made from natural gas the renewable content could be as high as 40% when using a SMR to generate the synthesis gas. The Fischer Tropsch and renewable products both require further processing with hydrogen to make finished products.

The upgrading of these products can be done together or separate. The Fischer Tropsch products to be upgraded typically include paraffin hydrocarbons from C5 to C100. The long chain products C21+ can be cracked to middle distillate fuels or can be hydro processed to make waxes or lube base oils. For waxes and base oils it is desirable to minimize cracking in which case the heavy Fischer Tropsch products will be upgraded separately. If the target is middle distillate fuels the heavy Fischer Tropsch waxy products (C21+) may be co processed with the renewable feed. In either case the hydro processed product can be blended and distilled or kept separate and distilled into finished products. The final product upgrading configuration is defined by the product target specifications. The finished products, weather derived from natural gas or renewable feed, will be totally compatible and can be blended in any proportion with each other or with other petroleum derived products. Products that are co processed may result in renewable content of from 1% to 80%. When the renewable products are processed separately the renewable content of those products is 100%. However the separately processed GTL products will still have a small renewable content 1% to 40% due to utilization of the waste products from the renewable materials that are recycled to make additional synthesis gas.

The broad range of potential renewable content in the products is based on the range of excess hydrogen available depending on the configuration of the reforming section of the GTL plant and the ratio of renewable feedstock to Fischer Tropsch derived hydrocarbons available for hydro processing. A SMR can be operated efficiently to produce synthesis gas in an approximately 3:1 H2: CO ratio. The Fischer Tropsch reaction requires synthesis gas in approximately 2:1 ratio. Therefore in the case of a SMR there is substantial potential for excess hydrogen. This excess hydrogen is typically recycled and used as fuel in the SMR but could be used for downstream hydro processing resulting in a substantial volume of hydrogen available for hydro processing. In this case the amount of renewable feed could result in approximately three times as much renewable product as Fischer Tropsch product. Theoretically the SMR synthesis gas could be shifted to all hydrogen and then the plant would be strictly a hydrogen source that could process 100% renewable feed. That configuration is not part of the scope of the present invention. The objective of the present invention is to efficiently utilize a GTL plant to leverage additional production of renewable feedstocks. The advantage to the GTL plant is to reduce the CO2 footprint of the plant and utilize the infrastructure and hydrogen of the plant to produce additional products. This includes leveraging the waste products from hydro deoxygenating a renewable feed to produce additional synthesis gas for the Fischer Tropsch reaction, such products also being of a renewable nature. In the case of an ATR the amount of excess hydrogen is much less resulting in a renewable feed limit of about 50% of the Fischer Tropsch production. The renewable feed could also be less depending on availability hence the broad range. With the SMR being the practical limit of the present invention for excess hydrogen available for downstream processing and assuming the renewable feedstock is not limiting the maximum renewable content of a blended product is approximately 80%. If the products are hydro processed separately the Fischer Tropsch derived products could have approximately 40% renewable content due to recycling of waste components.

Co processing of the renewable feeds has been proposed by Mackay et al. in US Patent Publication No. 2011/0113676. In this reference municipal solid waste (MSW) is the primary feed. The MSW is refined to produce a refuse derived fuel (RDF) that is depleted of inorganics. The RDF is gasified to make synthesis gas. The synthesis gas is converted to a Fischer Tropsch raw product. Excess hydrogen is used to upgrade a combined Fischer Tropsch product and a triglyceride feed.

The present invention differs from the Mackay reference in that it is based on reforming natural gas. Natural gas by nature has a high hydrogen to carbon ratio. The result is that efficiently reforming the gas provides a H2: CO ratio greater than required by the Fischer Tropsch reaction. The excess hydrogen can efficiently be utilized for downstream processing without sacrificing efficiency in the GTL portion of the plant. In the case of MSW, as with most biomass resources, the nature of the feed is deficient in hydrogen. Therefore the gasifier is operated with excess water in the feed to produce a higher H2: CO ratio. While there may be operational advantages to the high water feed it is not optimum from a carbon standpoint. Also, while the hydrogen derived from natural gas is not renewable it is much easier to clean. The contaminants found in MSW are more numerous and difficult to remove resulting in contaminated synthesis gas. In the case of natural gas reforming, the reformer can operate at 20-40 bars sufficient to pass directly to the Fischer Tropsch reactor without further compression. It is highly unlikely that the MSW gasification can operate at these pressures as the feed system to transfer irregular shaped solids to the gasifier at pressure is not practical.

The Mackay process does not take advantage of recycling waste products from hydro processing of renewable feeds. The Mackay process also does not find advantage to the reduced CO2 footprint enjoyed by the present invention as the nature of the Mackay primary feed is considered to be renewable.

Co processing of renewable feeds is taught by Knuuttila in US Patent Publication No. 2010/0317903. In this reference a biological feed is gasified to make synthesis gas. The synthesis gas is converted to Fischer Tropsch hydrocarbon products. The Fischer Tropsch hydrocarbon product is hydro processed and a separate bio oil is also hydro processed. The Fischer Tropsch products and hydro processed bio oils are combined and fractionated.

The present invention differs from the Knuuttila reference in that synthesis gas is generated by reforming natural gas whereas Knuuttila gasifies biomass. In the present invention excess hydrogen is efficiently extracted from the synthesis gas for downstream hydro processing whereas Knuuttila produces hydrogen in a separate reformer by reforming waste components or imported methanol, recognizing that the biomass feed stream is deficient in hydrogen. The Knuuttila design gains no advantage of reduced carbon footprint enjoyed by the present invention as it utilizes biological feed.

Gasification of a carbonaceous feed is taught by Blevins et al. in US 2011/0178185. While the carbonaceous feed is clearly directed at renewable biomass natural gas is included in the definition of carbonaceous feed. Unlike the present invention this reference does not teach efficient extraction of hydrogen for downstream processing of renewable feeds or co processing of such streams.

The present invention is directed to a process to efficiently utilize resources such as hydrogen and infrastructure of a Gas to Liquids process to efficiently co process renewable fats and oils or polymers. Such processing enhances the GTL operation by reducing the carbon footprint, adding a small amount of renewable material into the Fischer Tropsch product and adding a new renewable product in a very capital and energy efficient manner.

SUMMARY OF THE INVENTION

Renewable feedstocks containing triglycerides and free fatty acids can be advantageously converted into fuels and chemicals in combination with a gas to liquids (GTL) process.

A known gas to liquids process has three main components:
1) Conversion of natural gas to syngas (H2+CO)
2) Conversion of syngas to hydrocarbons
3) Hydro processing of the synthesized hydrocarbons to make finished products The preferred method of the present invention is to use natural gas as the feed; however, it is within the scope of the process to use any carbonaceous feed. The syngas produced in the first step provides a source of hydrogen for the third step. This hydrogen may be removed by membrane or PSA (pressure swing adsorption). Only a small portion of the hydrogen is removed as required in the hydro processing step and to adjust the $H_2$:CO ratio for the Fischer Tropsch synthesis.

In the process of the present invention, the renewable natural feed material can be co processed with the synthesized oil. The processing may be in one reactor such as a hydrocracker or in separate reactors depending on whether it is desirable to end up with mixed products or separate products. It may also be desirable to process the renewable feed separate from the Fischer Tropsch derived feed as the Fischer Tropsch material is much heavier (except when the renewable feed is a polymer) and will require more hydrocracking, if for example, the desired product is a middle distillate fuel. If the renewable products are hydro processed separate from the synthesized products, the finished products may be blended or used separately and both may be blended together or separately with conventional crude oil derived products.

In all cases, a portion of the hydrogen produced in the first step of the GTL process is used to hydro process the synthesized product and the renewable feedstock.

Processing of renewable feedstocks in this manner results in the production of by products such as $H_2O$, CO, $CO_2$ propane and other light hydrocarbon byproducts. All or a portion of these byproducts can be advantageously recycled back to the first step of the GTL process to produce more synthesis gas.

When the synthesized products are co processed or blended with the renewable products the result is a unique composition of matter containing a blend of natural gas derived and renewable molecules. Products synthesized by the Fischer Tropsch reaction have a very uniform distribution of highly paraffinic molecules including even and odd carbon numbers. The hydrocarbon chains produced by Fischer Tropsch include very long waxy chains. When they are hydrocracked to produce a jet or diesel fuel the resulting product is distilled to the range required for the fuel. A diesel fuel for example has a carbon distribution with hydrocarbon chains ranging from about C10-C19. The hydrocracked material has paraffin and iso-paraffin molecules in this range.

When the feedstock is a triglyceride and/or fatty acids, the naturally occurring products have a narrow distribution of carbon number. Triglycerides have three fatty acid chains linked to a three carbon backbone with an oxygen molecule between each chain. The three side chains are even number carbon chains with a narrow distribution of chain length generally in the C16-C20 range with a significant distribution around C18.

When hydro processed, the oxygen molecules and the three carbon backbone of the triglyceride produce by product waste including $H_2O$, CO, $CO_2$ propane and other light hydrocarbons. As such, this represents loss of material from the feed that will not be in the final product. Also, to make a finished fuel the C18 product is in the diesel boiling range but it is a heavy diesel with a narrow distribution. The product can be improved with additional cracking and isomerization to get a full range diesel with improved cold flow properties. This cracking will result in production of some shorter chain material that is too light for diesel and therefore results in potential lower value (C5-C9) naphtha. However, these lighter products can also be recycled back to the reformer and converted to synthesis gas for further conversion to useful products.

When blended or co processed with the synthesized material which has a full boiling range there is less need to crack the renewable material.

Therefore, it can be advantageously processed to reduce the amount of light cracked material. Also, any light cracked material that is produced can be recycled to the first step to produce syngas that will be converted to product by Fischer Tropsch synthesis. The Fischer Tropsch synthetic material may therefore be composed of natural gas derived and renewable derived components.

The integrated process if co processed or blended will result in a unique product composition. In the case of a diesel product, for example, the highly predicable distribution from a Fischer Tropsch synthesis and hydrocracking will be modified, showing a spike in the C16-C18 carbon number range from the addition of the renewable feedstock.

The co processing and/or blending of the renewable product with a GTL process can be done at great advantage to get the maximum benefit of low cost hydrogen and efficient utilization of the renewable feedstock. This process efficiently utilizes the resources (hydrogen) and infrastructure of the GTL process. It also efficiently utilizes lower value waste by products of the co processed renewable feed such as propane by producing additional synthesis resulting in a reduced $CO_2$ footprint.

DETAILED DESCRIPTION OF THE PREFERRED EMBODIMENTS

The embodiments discussed herein are merely illustrative of specific manners in which to make and use the invention and are not to be interpreted as limiting the scope of the present invention.

Figure 1:
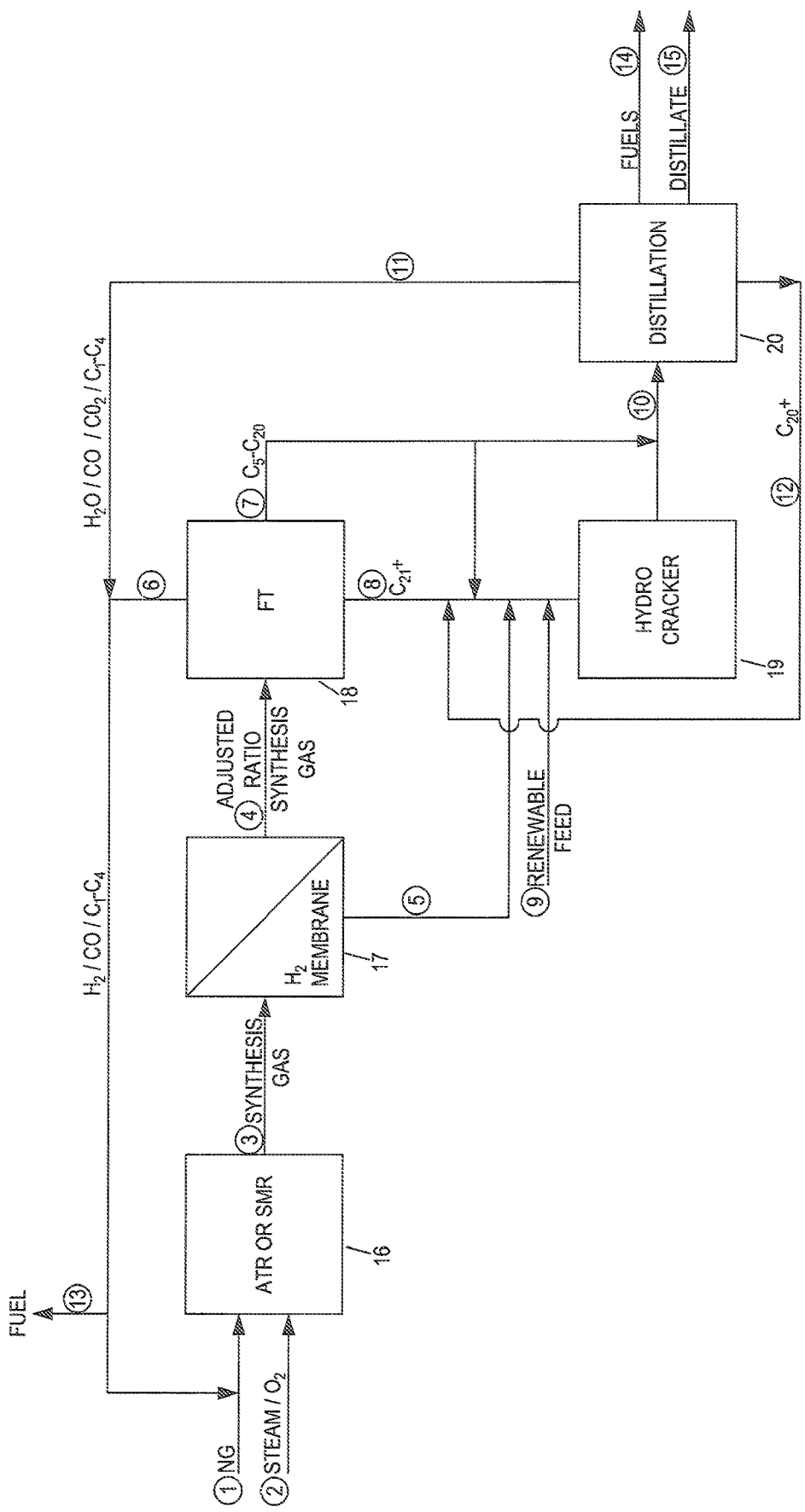
FIG. 1 is a process flow diagram of a preferred embodiment of the present invention.

In FIG. 1, natural gas stream 1 is fed with steam and oxygen stream 2 to reformer 16. The reformer is preferably an Autothermal Reformer. Synthesis gas stream 3 comprising Carbon Monoxide and hydrogen exits the reformer. The synthesis gas typically has a $H_2$: CO ratio of 2.2 to 2.6. The synthesis gas stream is separated into a hydrogen rich stream and a ratio adjusted stream in hydrogen membrane 17. The ratio adjusted stream 4 has a preferred ratio of about 2:1. This ratio may be further adjusted within the Fischer Tropsch unit 18 depending on the reactor configuration. The Fischer Tropsch unit 18 contains one or more Fischer Tropsch reactors configured in parallel and/or series with or without recycle to achieve the desired targets for conversion and selectivity. The reactor may be fixed bed, fluidized bed, ebulating bed, microchannel or slurry bubble column reactors. Any reactor known to one skilled in the art may be used. The reactors may be configured in a manner desirable to achieve the objective of converting synthesis gas to hydrocarbon products. The $H_2$:CO ratio may be adjusted within the Fischer Tropsch block to enhance performance such as hydrocarbon selectivity. Products from the Fischer Tropsch reactor may be separated a number of different ways. The figure describes three product streams. A light gaseous stream 6 which contains unreacted synthesis gas $H_2$, CO, $CO_2$, any inerts that entered in feed streams and light hydrocarbons primarily C1-C4. An intermediate liquid hydrocarbon stream 7 predominately C5-C20 hydrocarbons. This stream is very paraffinic but may contain significant amounts of olefins and alcohols. The concentration and distribution of non paraffinic hydrocarbons may vary significantly depending on the catalyst and operating conditions employed in the Fischer Tropsch reactors. A heavy hydrocarbon stream 8 containing predominately C21+ paraffinic hydrocarbons.

All or a portion of the intermediate liquid hydrocarbon stream 7 may be blended with the heavy hydrocarbon stream 8 and a renewable feed stream 9 for hydro processing in unit 19 which includes hydro cracking. Enriched hydrogen 5 is added to the hydro processing unit. This hydrogen may be further purified by Pressure Swing Adsorption, for example, before addition to unit 19. A portion of the intermediate liquid stream 7 may be bypassed around unit 19 to provide a small amount of primary alcohols as a lubricity improver in the finished product 15.

The hydro cracked product 10 is fed to distillation unit 20 for separation. The light gaseous stream 11 contains $H_2O$, CO, $CO_2$ and light hydrocarbons primarily C1-C4. Some of these products are produced as a result of decomposition of the renewable feed. This is particularly so for plant oils, crop oils and animal fats. In the case of polymers such as waste plastics the oxygen components such as $H_2O$, CO and $CO_2$ will not be present in appreciable amounts however light hydrocarbons can advantageously be recycled to reformer 16 by adding them into the reformer feed, resulting in a portion of the synthesis gas going to the Fischer Tropsch synthesis being of renewable origin.

A light paraffinic naphtha stream 14 is removed from the top of the distillation column. A middle distillate product 15 is removed from the side of the column. A heavy bottom cut 12 that is heavier than the desired end point of the middle distillate product is removed from the bottom of the column and recycled to the hydro processing unit 19. This product will be cracked to extinction.

The distillate product may preferably be a diesel product. If the diesel requires a low pore point it may be necessary to further hydrotreat and hydroisomerize one or more of the feed steams to increase the iso paraffin content of the products. All or a part of the straight run Fischer Tropsch liquid for example in the C9-C20 range can be fed into a hydrotreater and subsequently into a hydroisomerization reactor. This additional hydro processing improves the pour point of the final product allowing attainment of jet fuel specifications. One skilled in the art can make such adjustments depending on the product slate and target specifications.

Figure 2:
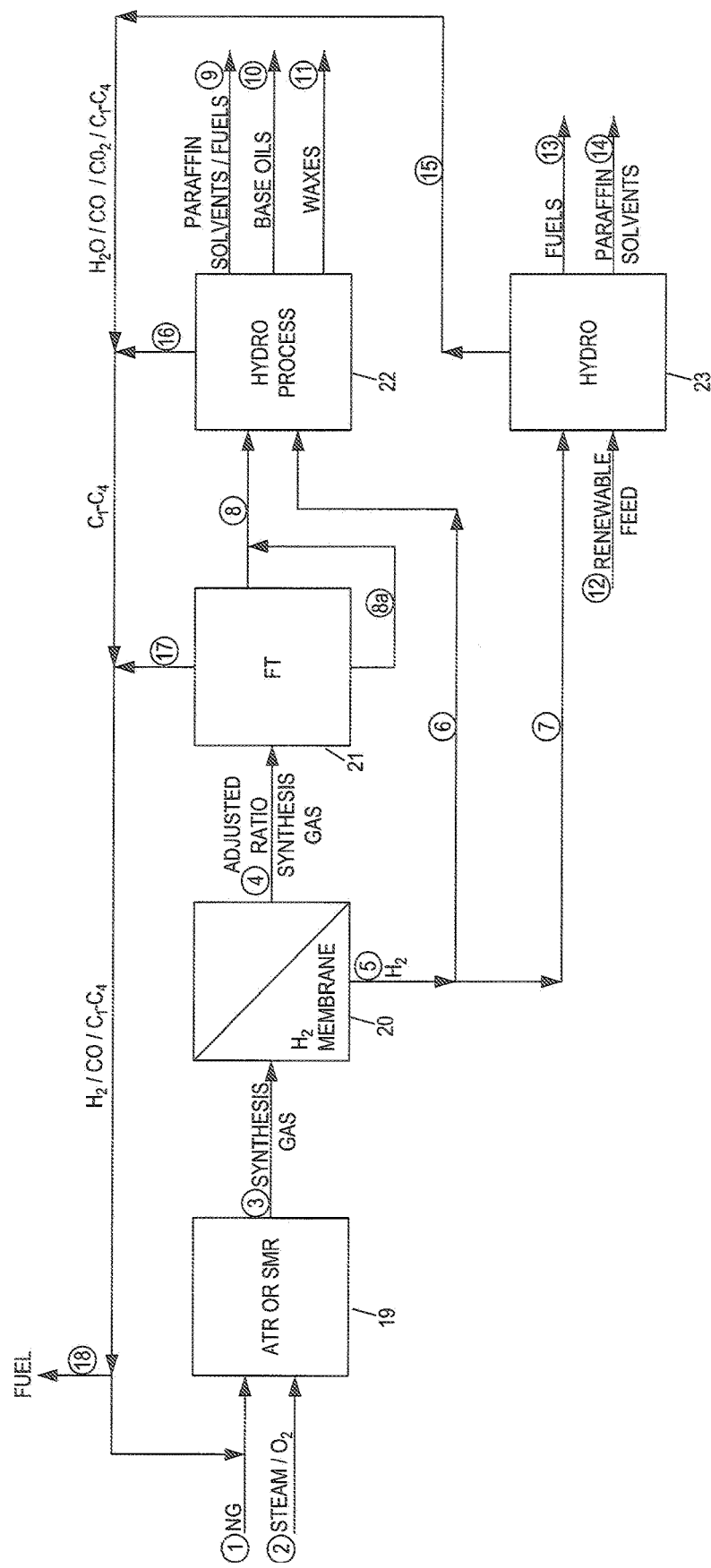
FIG. 2 is a process flow diagram of another preferred embodiment of the present invention.

In FIG. 2, natural gas stream 1 is fed with steam and oxygen stream 2 to reformer 19. The reformer is preferably an Autothermal Reformer. Synthesis gas stream 3 comprising Carbon Monoxide and hydrogen exits the reformer. The synthesis gas typically has a $H_2$: CO ratio of 2.2 to 2.6. The synthesis gas stream is separated into a hydrogen rich stream and a ratio adjusted stream in hydrogen membrane 20. The ratio adjusted stream 4 has a preferred ratio of about 2:1. This ratio may be further adjusted within the Fischer Tropsch unit 21 depending on the reactor configuration. The Fischer Tropsch unit 21 contains one or more Fischer Tropsch reactors configured in parallel and/or series with or without recycle to achieve the desired targets for conversion and selectivity. The reactors may be fixed bed, fluidized bed, ebulating bed, microchannel or slurry bubble column reactors. Any reactor known to one skilled in the art may be used. The reactors may be configured in a manner desirable to achieve the objective of converting synthesis gas to hydrocarbon products. The $H_2$: CO ratio may be adjusted within the Fischer Tropsch block to enhance performance such as hydrocarbon selectivity. Products from the Fischer Tropsch reactor may be separated a number of different ways. The figure describes three product streams. A light gaseous stream 17 which contains unreacted synthesis gas $H_2$, CO, $CO_2$, any inerts that entered in feed streams and light hydrocarbons primarily C1-C4. An intermediate liquid hydrocarbon stream 8 predominately C5-C20 hydrocarbons. This stream is very paraffinic but may contain substantial amounts of olefins and alcohols. The concentration and distribution of non paraffinic hydrocarbons may vary significantly depending on the catalyst and operating conditions employed in the Fischer Tropsch reactors. A heavy hydrocarbon stream 8a containing predominately C21+ paraffinic hydrocarbons.

The intermediate liquid hydrocarbon stream 8 and heavy hydrocarbon stream 8a can be processed together or separately in hydro processing block 22 depending on target product specifications. If paraffinic oils and waxes are the target products, the hydro processing is a simple hydro treating reactor used to saturate olefins. After distillation there may be need to polish one or more of the streams to enhance color. If the objective is to make base oils in unit 22 the operation will include a hydroisomerization reactor to increase the iso paraffin content of the feed stream. Again it may be necessary to polish one or more finished products to enhance color. Light hydrocarbons 16 generated by mild cracking in block 22 may be recycled to reformer 19 for producing additional synthesis gas or may be used as fuel gas 18. The hydrogen stream 5 extracted by membrane unit 20 is purified and split into stream 6 and 7. Stream 6 provides hydrogen for block 22 and stream 7 provides hydrogen necessary for hydro processing in block 23 with renewable feed stream 12. If the renewable feed is a plant oil, crop oil, algae oil animal fat or waste grease with substantial amounts of triglycerides it will be hydro deoxygenated in block 23 resulting in production of $H_2O$, CO, $CO_2$ and C1-C4 hydrocarbons. These waste products stream 15 can be recycled to reformer 19 to produce additional synthesis gas. The hydrocarbon products can be saturated and used as paraffin solvents 14 or subjected to additional hydroisomerization in block 23 to produce jet and diesel fuels 13. If the renewable feed 12 is a polymer such as a waste plastic it may be hydro cracked to fuels, saturated to make paraffin oils or waxes or hydroisomerized to make base oils.

The products from block 22 and block 23 may be blended or kept separate. The products are compatible with petroleum derived products and may be blended with them in any proportion.

In this configuration the products from block 23 are totally renewable while the products from block 22 are only partially renewable.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes of exemplification.

A non-limiting example is illustrative of the process of the present invention.
Example Natural Gas (11.0MMSCFD) was reacted in an Autothermal Reformer with 6.8 MMSCFD of 93% oxygen to produce 31.9 MMSCFD of synthesis gas of the following composition.

Component Mol %
$H_2$ 62.02
CO 28.03
$CO_2$ 6.31
Ar 0.93
$N_2$ 1.34
$C_1$ 1.37

A hydrogen membrane was used to extract approximately 1.9MMSCFD of hydrogen from the synthesis gas stream. The hydrogen was optionally purified and compressed for later use in the product refining section of the plant.

The synthesis gas, after hydrogen extraction was reacted over a cobalt Fischer Tropsch catalyst in multiple stages to a CO conversion of approximately 92%, resulting in the production of 1,000 BPD of a synthetic crude product. The synthetic crude is collected in separators as a heavy Fischer Tropsch liquid (wax 700 BPD) and a light Fischer Tropsch liquid (oil 300 BPD).

The heavy syncrude is blended with a portion of the light syncrude and approximately 500 BPD of clean degummed jatropha oil. This mixture was fed to a hydro cracker along with the 1.9 MMSCFD of hydrogen extracted from the synthesis gas to crack the heavy synthetic waxy components and decompose the triglycerides of the Jatropha oil. The combined product is fed to a distillation column. A paraffinic naphtha product (300 BPD) was collected from the column overhead. A diesel boiling range product (1,150 BPD) was collected from the side of the column. This product is approximately $\frac{1}{3}^{Rd}$ renewable. Hydrocarbons heavier than the end point of diesel are drawn off the bottom of the distillation column and recycled to the feed tank. Heavy components are recycled to extinction so that only naphtha and diesel boiling range products are collected. Light hydrocarbons, $H_2O$, CO, $CO_2$ and hydrogen are purged from the recycle gas. A portion of the purged gas stream was recycled to the Autothermal Reformer to produce more synthesis gas. The balance of the purge stream is used as fuel.

Whereas, the present invention has been described in relation to the drawings attached hereto, it should be understood that other and further modifications, apart from those shown or suggested herein, may be made within the spirit and scope of this invention.

What is claimed is:

1. A reduced $CO_2$ footprint gas to liquids process comprising;
    a) converting natural gas to synthesis gas comprising $H_2$ and CO;
    b) separating the synthesis gas into a hydrogen rich stream and a ratio adjusted synthesis gas stream;
    c) converting the ratio adjusted synthesis gas stream to hydrocarbons in a Fischer Tropsch reaction;
    d) upgrading the Fischer Tropsch products and a renewable feed with the hydrogen rich stream of step b) to produce hydrocarbon products;
    e) thereafter converting waste products from hydro processing of the renewable feed to synthesis gas comprising $H_2$ and CO; and
    f) subjecting the synthesis gas produced in step e) to the separating of step b), the Fischer Tropsch reaction of step c), and the upgrading of step d).

2. The process according to claim 1 wherein the renewable feed stock material includes seed oils, crop oils, animal fats, recycled greases and oils, algae oils and recycled plastics.

3. The process according to claim 1 wherein the hydrogen stream of step b) is further purified to increase hydrogen purity.

4. The process according to claim 1 wherein synthesis gas is produced in an Autothermal Reformer.

5. The process according to claim 1 wherein synthesis gas is produced in a Steam Methane Reformer.

6. The process according to claim 1 wherein the synthesized hydrocarbon products and the renewable products may be blended together in any ratio and may be blended together or separate with other hydrocarbon products in any ratio.

7. The process according to claim 1 wherein the renewable feed is processed in the same hydro processing unit and/or distillation unit resulting in blended Fischer Tropsch and renewable products.

8. The process according to claim 1 wherein the renewable feed is processed in separate hydro processing and distillation units resulting in separate Fischer Tropsch and renewable product.

9. The process according to claim 1 where the hydrocarbon products include jet, diesel or jet and diesel blend stocks, synthetic crude, paraffin oils, paraffin waxes, base oils and naphtha.

10. The process according to claim 1 wherein the Fischer Tropsch reactor is a fixed bed, fluidized bed, ebulating bed, microchannel or slurry bubble column reactor.

11. The process according to claim 1 wherein the catalyst utilized in the Fischer Tropsch reaction is an Iron based or Cobalt based catalyst.

12. The process according to claim 1 wherein any of the hydrocarbon products may be subjected to additional hydro processing or filtering processes to enhance color, stability or performance.

\* \* \* \* \*